United States Patent [19]
Bondinell et al.

[11] Patent Number: 5,599,810
[45] Date of Patent: Feb. 4, 1997

[54] FURO- AND THIENO[4,3,2-EF][3]BENZAZEPINES USEFUL AS ALPHA ADRENERGIC RECEPTOR ANTAGONISTS

[75] Inventors: William E. Bondinell, Wayne; Robert M. Demarinis, Ardmore; Thomas W. Ku, Dresher, all of Pa.; Francis R. Pfeiffer, Cinnaminson, N.J.; Dinubhai H. Shah, Blue Bell; Joseph W. Venslavsky, Wayne, both of Pa.

[73] Assignee: SmithKline Beecham Corporation, Philadelphia, Pa.

[21] Appl. No.: 505,297

[22] Filed: Oct. 20, 1995

Related U.S. Application Data

[63] Continuation of Ser. No. 17,713, Feb. 16, 1993, abandoned.

[51] Int. Cl.$^6$ ............... A61K 31/55; C07D 491/06; C07D 495/06
[52] U.S. Cl. ............................. 514/217; 540/581
[58] Field of Search ............. 540/581; 514/217

[56] References Cited

U.S. PATENT DOCUMENTS

| | | | |
|---|---|---|---|
| 4,957,914 | 9/1990 | Clark et al. | 514/217 |
| 4,959,360 | 9/1990 | Lafferty et al. | 514/217 |
| 4,963,547 | 10/1990 | Lafferty et al. | 514/217 |
| 4,978,660 | 12/1990 | Lafferty et al. | 514/215 |
| 5,006,521 | 4/1991 | Lafferty et al. | 514/215 |

*Primary Examiner*—Philip I. Datlow
*Attorney, Agent, or Firm*—Mary E. McCarthy; Stephen Venetianer; Edward T. Lentz

[57] ABSTRACT

Alpha-adrenergic receptor antagonsists having the formula (I) as set forth below which are useful to produce alpha-adrenergic antagonism, pharmaceutical compositions thereof, and methods of treatment therewith are disclosed:

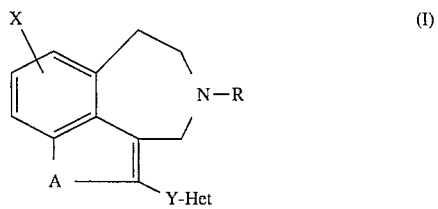

The variables X, R, Y, Het and A are as defined in the specification.

24 Claims, No Drawings

FURO- AND THIENO[4,3,2-EF][3]BENZAZEPINES USEFUL AS ALPHA ADRENERGIC RECEPTOR ANTAGONISTS

This application is a 35 USC 371 national stage application of international application PCT/US94/01739 filed Feb. 16, 1994, which is a continuation of U.S. application Ser. No. 08/017,713 filed Feb. 16, 1993, now abandoned.

FIELD OF THE INVENTION

This invention relates to novel 2-substituted-3,4,5,6-tetrahydrothieno- or tetrahydrofuro-[4,3,2-ef][3]benzazepine compounds having α-adrenergic receptor antagonist activity.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of agonists and antagonists, the a adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, J. Med. Chem., 25, 1389 (1982)). Experiments using 6-chloro-9-(3-methyl-2-butenyloxy)-3-methyl-2,3,4,5-tetrahydro-1H-3-benzazepine (SK&F 104078) demonstrated that the classical adrenoceptors are heterogeneous and can be divided into SK&F 104078-insensitive and SK&F 104078-sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, Jul. 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with a adrenoceptors include methyldopa, clonidine, and prazosin. Efforts to modulate sympathetic tone through interactions with a adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methyl-norepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. Nos. 3,833,591, 3,904,645, and 3,906,000 disclose substituted compounds of the following base structure:

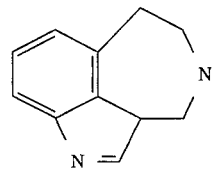

These compounds are useful as hypoglycemic agents.

PCT Application Number WO 87/00522 describes a series of 4-aminotetrahydrobenz[c,d]indoles and tetrahydroazepino[3,4,5-c,d]indoles having the general formula:

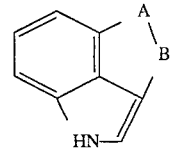

in which A-B is —CH$_2$—CH(NRR)—CH$_2$ or —CH$_2$—CH$_2$—NR—CH$_2$. These compounds are flopamine agonists useful as hypotensives.

U.S. Pat. No. 4,957,914 and PCT Application No. WO 92/05157 describe certain 1,9alkano-bridged-2,3,4,5-tetrahydro-1H-3-benzazepines useful in the treatment of CNS disorders.

U.S. Pat. Nos. 5,006,521, 4,978,660, 4,963,547, and 4,959,360 disclose substituted 3,4,5,6-tetrahydrothieno- and tetrahydrofuro-[4,3,2-ef][3]benzazepines. These compounds are α-adrenergic receptor antagonists.

SUMMARY OF THE INVENTION

The present invention resides in the discovery that certain 2-substituted-3,4,5,6-tetrahydrothieno- and tetrahydrofuro-[4,3,2-ef][3]benzazepine compounds are α-adrenoceptor antagonists. Presently preferred compounds of the invention include, but are not limited to, the following:

5-(7-chloro-3,4,5,6-tetrahydro-4-methylthieno[4,3,2-ef][3]benzazepin-2-yl)oxazole;

5-(7-chloro-3,4,5,6-tetrahydro-4-methylfuro[4,3,2-ef][3]benzazepin-2-yl)oxazole;

2-(7-chloro-3,4,5,6-tetrahydro-4-methylfuro[4,3,2-ef][3]benzazepin-2-yl)-4,5-dihydro-1H-imidazole;

4-chloro-1-[(7-chloro-3,4,5,6-tetrahydro-4-methylfuro[4,3,2-ef][3]benzazepin-2-yl)methyl]-1H-pyrazole;

4-chloro-1-[3-(7-chloro-3,4,5,6-tetrahydro-4-methylfuro[4,3,2-ef][3]benzazepin-2-yl)propyl]-1H-pyrazole;

(E)-3-[(7-chloro-3,4,5,6-tetrahydro-4-methylfuro[4,3,2-ef][3]benzazepin-2-yl)methylene]dihyrdro-2(3H)furanone;

3-[(7-chloro-3,4,5,6-tetrahydro-4-methylfuro[4,3,2-ef][3]benzazepin-2-yl)methylene]-2-pyrrolidinone;

1-[3-(7-chloro-3,4,5,6-tetrahydro-4-methylfuro[4,3,2,-ef][3]benzazepin-2-yl)-1-oxo-2-propenyl]pyrrolidine;

(E)-1-[[2-(7-chloro-3,4,5,6-tetrahydro-4-methylfuro[4,3,2,-ef][3]benzazepin-2-yl)ethenyl]sulfonyl]pyrrolidine;

2-[2-(7-chloro-3,4,5,6-tetrahydro-4-methylfuro[4,3,2-ef][3]benzazepin-2-yl)-2-oxoethyl]-4,5-dihydro-4,4-dimethyloxazole;

2-[2-(7-chloro-3,4,5,6-tetrahydro-4-methylfuro[4,3,2-ef][3]benzazepin-2-yl)-2-hydroxyethyl]-4,5-dihydro-4,4-dimethyloxazole;

2-[2-(7-chloro-3,4,5,6-tetrahydro-4-methylfuro[4,3,2-ef][3]benzazepin-2-yl)ethenyl]-4,5-dihydro-4,4-dimethyloxazole;

2-[2-(7-chloro-3,4,5,6-tetrahydro-4-methylthieno[4,3,2-ef]
[3]benzazepin-2-yl)-2-oxoethyl]-4,5-dihydro-4,4-dimethyloxazole;

2-[2-(7-chloro-3,4,5,6-tetrahydro-4-methylfuro[4,3,2-ef][3]
benzazepin-2-yl)-2-oxoethyl]-4,5-dimethyloxazole;

2-[2-(7-chloro-3,4,5,6-tetrahydro-4-methylfuro[4,3,2-ef][3]
benzazepin-2-yl)-2-hydroxyethyl-4,5-dimethyloxazole;

2-[2-(7-chloro-3,4,5,6-tetrahydro-4-methylfuro[4,3,2-ef][3]
benzazepin-2-yl)ethenyl]-4,5-dimethyloxazole;

4-chloro-1-[2-(7-chloro-3,4,5,6-tetrahydro-4-methylfuro[4,
3,2-ef][3]benzazepin-2-yl)methoxy]methyl]-1H-pyrazole;

(4-chloro-1H-pyrazol-1-yl)methyl 7-chloro-3,4,5,6-tetrahydro-4-methylfuro[4,3,2-ef][3]benzazepine-2-carboxylate;

2-[2-(7-chloro-3,4,5,6-tetrahydro-4-methylfuro[4,3,2-ef][3]
benzazepin-2-yl)-2-hydroxyethyl]pyridine;

7-chloro-3,4,5,6-tetrahydro-4-methyl-2-[(2-pyridinyl-
methoxy)methyl]furo[4,3,2-ef][3]benzazepine;

7-chloro-2-[[(4-chloro-2-pyridinyl)methoxymethyl]-3,4,5,
6-tetrahydro-4-methylfuro[4,3,2-ef][3]benzazepine;

7-chloro-3,4,5,6-tetrahydro-4-methyl-2-[(3-pyridinyl-
methoxy)methyl]furo[4,3,2-ef][3]benzazepine;

7-chloro-3,4,5,6-tetrahydro-4-methyl-2-[(4-pyridinyl-
methoxy)methyl]furo[4,3,2-ef][3]benzazepine;

2-pyridinylmethyl 7-chloro-3,4,5,6-tetrahydrofuro-4-methylfuro[4,3,2-ef][3]benzazepine-2-carboxylate;

2-[2-(7-chloro-3,4,5,6-tetrahydro-4-methylfuro[4,3,2-ef][3]
benzazepin-2-yl)-2-hydroxyethyl]benzoxazole;

2-[2-(7-chloro-3,4,5,6-tetrahydro-4-methylfuro[4,3,2-ef][3]
benzazepin-2-yl)ethenyl]benzoxazole;

2-[2-(7-chloro-3,4,5,6-tetrahydro-4-methylfuro[4,3,2-ef][3]
benzazepin-2-yl)-2-oxoethyl]benzothiazole;

2-[2-(7-chloro-3,4,5,6-tetrahydro-4-methylfuro[4,3,2-ef][3]
benzazepin-2-yl)-2-hydroxyethyl]benzothiazole;

2-[2-(7-chloro-3,4,5,6-tetrahydro-4-methylfuro[4,3,2-ef][3]
benzazepin-2-yl)ethenyl]benzothiazole;

N-(2-benzothiazolyl)-7-chloro-3,4,5,6-tetrahydro-4-methylfuro[4,3,2-ef][3]benzazepine-2-carboxamide; and 2-[(7-chloro-3,4,5,6-tetrahydro-4-methylfuro[4,3,2-ef][3]
benzazepin-2-yl)methylamino]benzothiazole;

or a pharmaceutically acceptable salt thereof.

The most preferred compound of the invention is 5-(7-chloro-3,4,5,6-tetrahydro-4-methylthieno[4,3,2-ef][3]benzazepin-2-yl)oxazole or a pharmaceutically acceptable salt thereof.

In a further aspect of the invention there are provided methods of antagonizing α-adrenoceptors in mammals, including humans, that comprise administering internally to a subject an effective amount of a 2-substituted-3,4,5,6-tetrahydrothieno[4,3,2-ef][3]benzazepine or a 2-substituted-3,4,5,6-tetrahydrofuro[4,3,2-ef][3]benzazepine compound.

Included in the present invention are pharmaceutical compositions comprising compounds useful in the method of the invention and a suitable pharmaceutical carrier. Preferably, these compositions are used to produce α adrenoceptor antagonism and contain an effective amount of compounds useful in the methods of the invention.

DETAILED DESCRIPTION OF THE INVENTION

The presently invented compounds that are α- adrenoceptor antagonists or are useful in preparing α- adrenoceptor antagonists are represented by the following Formula (I):

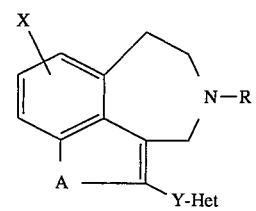

in which:

X is H, Cl, Br, F, I, $CF_3$, $C_{1-6}$ alkyl, $COR^1$, $CO_2R^2$, $CONR^2R^2$, CN, $NO_2$, $NR^2R^3$, $OR^3$, $SC_{1-4}$ alkyl, $S(CH_2)_{0-6}$ phenyl, $SCF_3$, or any accessible combination thereof of up to three substituents;

R is H, $C_{1-6}$ alkyl, or $C_{3-5}$ alkenyl;

each $R^1$ independently is $C_{1-6}$ alkyl or $(CH_2)_{0-6}$ phenyl;

each $R^2$ independently is H, $C_{1-6}$alkyl, or $(CH_2)_{0-6}$phenyl;

each $R^3$ independently is H, $C_{1-6}$ alkyl, $(CH_2)_{0-6}$phenyl, $COR^1$, or $SO_2R^1$;

A is O or S;

Y is a single bond, $-(CH_2)_{1-4}-$, $-CH=$, $-CH=CH-Q-$, or $-(CH_2)_{0-2}-E-(CH_2)_{0-2}-$;

Q is a single bond, $-SO_2-$ or $-C(O)-$;

E is $-CH(OH)-$, $-C(O)-$, $-O-$, $-S-$, $-CO_2-$, $-NR^2-$, or $-C(O)NR^2-$; and Het is a stable 5- to 7-membered monocyclic or 7- to 10-membered bicyclic heterocyclic ring, which is either saturated or unsaturated, and which consists of carbon atoms and from one to three heteroatoms selected from the group consisting of N, O, S, wherein the nitrogen and sulfur atoms may optionally be oxidized, and the nitrogen heteroatom may optionally be quaternized, and the carbon atoms may optionally be doubly bonded to oxygen, and including any bicyclic group in which any of the above-defined heterocyclic rings is fused to a benzene ring and wherein the Het is unsubstituted or substituted by any accessible combination thereof of up to three substituents selected from the group consisting of $C_1-C_6$alkyl, $C_1-C_6$alkoxy, Cl, Br, F, I, $CF_3$ $NR^2R^2$, $CO_2R^2$, $CONR^2R^2$, $SO_3H$, $SO_2NHR^2$, OH, $NO_2$, $SO_2C_1-C_6$alkyl, $SC_1-C_6$alkyl, or $NR^2COC_1-C_6$alkyl; or a pharmaceutically acceptable salt thereof.

As used herein $C_{1-6}$alkyl means straight or branched alkyl of one to six carbon atoms, $C_{3-5}$alkenyl means a straight or branched chain alkenyl having from 3 to 5 carbon atoms, and "any accessible combination thereof" means any combination of up to three substituents on the phenyl moiety that is available by chemical synthesis and is stable.

Formula (Ia) includes presently preferred Formula (I) compounds:

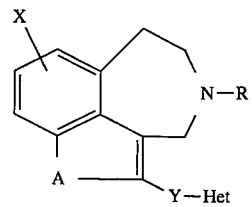

in which:

X is H, Cl, Br, F, I, $CF_3$, $C_{1-6}$ alkyl, $COR^1$, $CO_2R^2$, $CONR^2R^2$, CN, $NO_2$, $NR^2R^3$, $OR^3$, $SC_{1-4}$ alkyl, $S(CH_2)_{0-6}$ phenyl, or $SCF_3$;

R is H, $C_{1-6}$ alkyl, or $C_{3-5}$ alkenyl;

each $R^1$ independently is $C_{1-6}$ alkyl or $(CH_2)_{0-6}$ phenyl;

each $R^2$ independently is H, $C_{1-6}$alkyl, or $(CH_2)_{0-6}$phenyl;
each $R^3$ independently is H, $C_{1-6}$ alkyl, $(CH_2)_{0-6}$phenyl, $COR^1$, or $SO^2R^1$;
A is O or S;
Y is a single bond, —$(CH_2)_{1-4}$—, —CH=, —CH=CH—Q—, or —$(CH_2)_{0-2}$—E—$(CH_2)_{0-2}$—;
Q is a single bond, —$SO_2$— or —C(O)—;
E is —CH(OH)—, —C(O)—, —O—, —S—, —$CO_2$—, —$NR^2$—, or —$C(O)NR^2$—; and
Het is a stable 5- to 7-membered monocyclic or 7- to 10-membered bicyclic heterocyclic ring, which is either saturated or unsaturated, and which consists of carbon atoms and from one to three heteroatoms selected from the group consisting of N, O, S, wherein the nitrogen and sulfur atoms may optionally be oxidized, and the nitrogen heteroatom may optionally be quarternized, and the carbon atoms may optionally be doubly bonded to oxygen, and including any bicyclic group in which any of the above-defined heterocyclic rings is fused to a benzene ring and wherein the Het is unsubstituted or substituted by any accessible combination thereof of up to three substituents selected from the group consisting of $C_1$–$C_6$alkyl, $C_1$–$C_6$alkoxy, Cl, Br, F, I, $CF_3$ $NR^2R^2$, $CO_2R^2$, $CONR^2R^2$, $SO_3H$, $SO_2NHR^2$, OH, $NO_2$, $SO_2C_1$-$C_6$alkyl, $SC_1$-$C_6$alkyl, or $NR^2COC_1$-$C_6$alkyl; or a pharmaceutically acceptable salt thereof.

Preferred compounds are represented by Formula (Ia) when:

X is Cl, Br, F, or I;
R is $C_{1-6}$alkyl; and
Het is oxazolyl, dihydrooxazolyl, pyridinyl, benzothiazolyl, benzoxazolyl, indolyl, benzimidazolyl, imidazolyl, dihydroimidazolyl, pyrrolidinyl, pyrrolidin-one-yl, pyrrolyl, thienyl, furanyl, tetrahydrofuranyl, oxotetrahydrofuranyl, pyrazolyl, triazolyl, pyridazinyl, pyrimidinyl, pryazinyl, thiazolyl, tetrazolyl, benzofuranyl, benzothienyl, quinolyl, or isoquinolyl and each Het is unsubstituted or substituted by any accessible combination thereof of up to two substitutents selected from the group consisting of $C_{1-6}$alkyl, Cl, Br, F, I, or $CF_3$.

Also included in this invention are complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

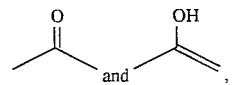

each tautomeric form is contemplated as being included within this invention whether existing in equilibrium or locked in one form by appropriate substitution. The meaning of any substituent at any one occurrence is independent of its meaning, or any other substituent's meaning, at any other occurrence, unless specified otherwise.

The starting substituted 3,4,5,6-tetrahydrothieno- and tetrahydrofuro-[4,3,2-ef][3]benzazepines used in the preparation of Formula (I) compounds are known to the art and are synthesized by the procedures detailed in U.S. Pat. Nos. 4,959,360 and 4,963,547. Reference should be made to such patents for their disclosure, which are incorporated herein by reference, for the preparation of said starting materials.

Scheme I

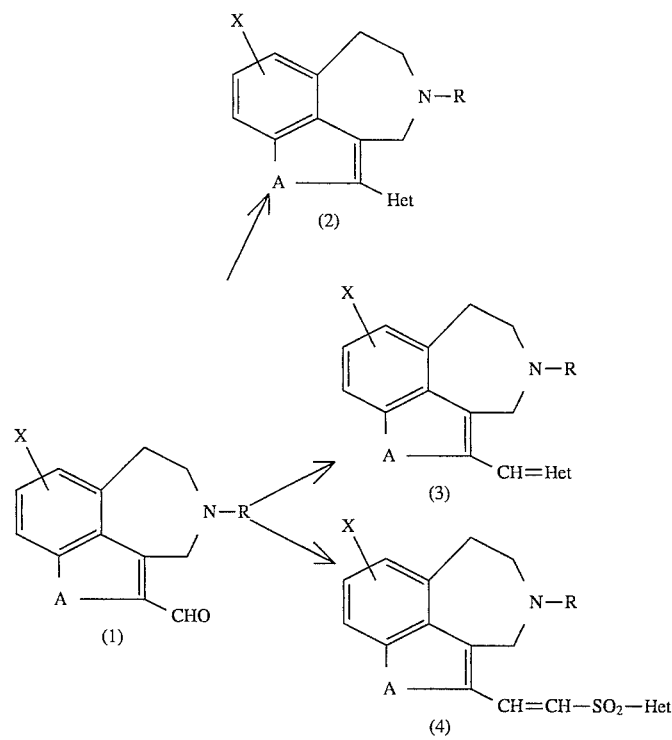

-continued
Scheme I

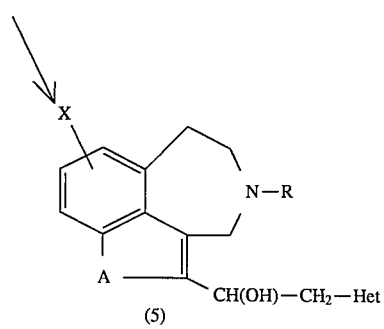

(5)

Scheme I shows the synthesis for Formula (I) compounds in which the Y-spacer group is a single bond, —CH=, —CH=CH—Q—, wherein —Q— is —SO$_2$— or —E—CH$_2$—, wherein E is —CH(OH)—. According to Scheme I, the 2-carboxaldehyde formula (1) compound is reacted with an appropriate heterocyclic-forming reagent, such as tosylmethylisocyanide, under suitable conditions, such as in the presence of base, for example, in the presence of potassium carbonate, in an appropriate solvent, such as in methanol, to give formula (2) compounds, which are Formula (I) compounds wherein the Het, for example an oxazolyl group, group is directly attached at the 2-position of the 3,4,5,6-tetrahydrothieno- or tetrahydrofuro-[4,3,2-ef][3]benzazepine ring system.

It should be appreciated by those skilled in the art that the selection of the appropriate heterocyclic-forming reagent determines which heterocyclic group is formed. For example, when the Het group is pyridine, the formula (1) aldehyde may be reacted with a β-ketoester or other activated methylene compound in the presence of ammonia. When the Het group is pyrimidine, the formula (1) aldehyde may be reacted with a 1,3-diketone and ammonia under oxidative conditions. Furthermore, when the aldehyde is modified, for example by reacting the aldehyde with an amine to generate the corresponding imine, subsequent reaction with a heterocyclic-forming reagent, such as tosylmethylisocyanide, under suitable conditions, such as in the presence of base, for example in the presence of potassium carbonate, gives additional heterocyclic groups, such as an imidazolyl group. [See T. L. Gilchrist, *Heterocyclic Chemistry*, Pitman Publishing (1985).]

Formula (I) compounds wherein Y is —CH=, which are Scheme I, formula (3) compounds are prepared by reacting the 2-carboxaldehyde formula (1) compound with a heterocycle bearing an acidic hydrogen, such as N-acetyl-2-pyrrolidinone, in the presence of a base, such as sodium hydride, or with a phosphonate carbanion generated by treating a phosphonic ester, such as α-diethylphosphono-α-butyrolactone, with a base, such as sodium hydride, n-butyllithium or lithium ethoxide, preferably sodium hydride.

Formula (I) compounds wherein Y is —CH=CH—Q—, in which Q is —SO$_2$—, which are Scheme I, formula (4) compounds, are prepared by reacting the formula (1) aldehyde compound with a phosphonate carbanion, generated by treating a phosphonic ester, such as [(diethylphosphono)methyl]sulfonylpyrrolidine, with a base, such as sodium hydride.

Formula (I) compounds wherein Y is —E—CH$_2$—, in which E is —CH(OH)—, which are Scheme I, formula (5) compounds are prepared by reacting the formula (1) aldehyde compound with a carbanion, such as the carbanion generated when a heterocycle, for example, 2-picoline, 2-methylbenzoxazole, or 2-methylbenzothiazole, is treated with a base, such as n-butyllithium. The formula (5) alcohol compound may then be converted to the corresponding vinyl compound by reacting the alcohol with methanesulfonyl chloride in the presence of a base, preferably triethylamine.

Scheme II

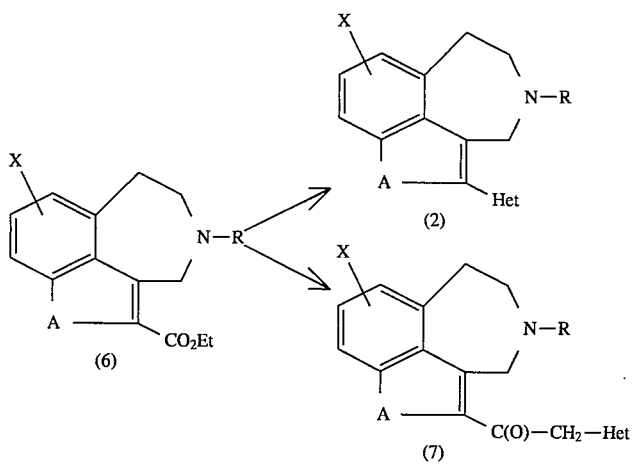

Scheme II shows the synthesis of Formula (I) compounds in which the Y-spacer group is a single bond or —E—$CH_2$—, wherein E is —C(O)—. According to Scheme II, the 2-$CO_2$Et compound of formula (6) is reacted with an appropriate heterocyclic-forming reagent, such as ethylenediamine, to give formula (2) compounds, which are Formula (I) compounds wherein the Het is directly attached to the tetrahydrothieno- or tetrahydrofuro-benzazepine ring system. Also according to Scheme II, the 2-$CO_2$Et formula (6) compound is reacted with a carbanion, such as the carbanion generated when a heterocycle, such as 4,5-dihydro-2,4,4-trimethyloxazole, 2,4,5-trimethyloxazole, or 2-methylbenzothiazole, is treated with a base, such as n-butyllithium, to give formula (7) ketone compounds. The formula (7) compounds may be converted to the corresponding hydroxy compounds, which are Scheme I, formula 5 compounds, using a suitable reducing agent such as sodium borohydride.

Scheme III

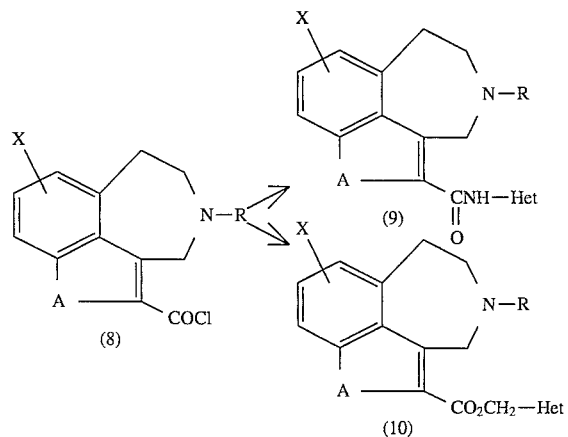

Scheme III shows the synthesis of Formula (I) compounds in which the Y-spacer group is —E—$(CH_2)_{0-1}$— wherein E is —C(O)NH— or —$CO_2$—. According to Scheme III, the formula (8) acid chloride compound reacts with an amine, such as 2-aminobenzothiazole, to give the formula (9) amide compounds. The amide compounds may then be converted to the corresponding amine compounds wherein Y is —$CH_2$—E—, in which E is —NH—, using an appropriate reducing agent, such as lithium aluminum hydride, in a suitable solvent, such as tetrahydrofuran. Also according to Scheme III, the acid chloride of formula (8) may be used to acylate an alcohol, such as 4-chloro-1H-pyrazole-1-methanol or 2-pyridinylmethanol, in the presence of a base, such as triethylamine, in a suitable solvent, such as tetrahydrofuran, to give formula (10) compounds.

Acid chlorides may also be used to prepare compounds containing other Y-spacer groups. For example, (E)-3-(7-chloro-3,4,5,6-tetrahydro-4-methylfuro[4,3,2-ef][3]benzazepin-2-yl)-2-propenoyl chloride is reacted with a nitrogen-containing heterocycle, such as pyrrolidine, in the presence of a base, such as dimethylformamide, to give compounds wherein Y is —CH=CH—Q—, in which Q is —C(O)—.

Scheme IV

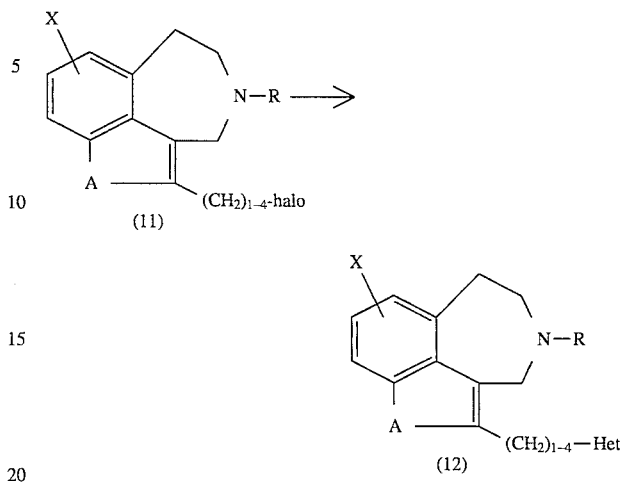

Scheme IV shows the synthesis of compounds in which the Y-spacer group is —$(CH_2)_{1-4}$—. According to Scheme IV, a 2-haloalkyl compound of formula (11), such as 2-bromomethyl-7-chloro-4-ethoxycarbonyl-3,4,5,6-tetrahydrofuro[4,3,2-ef][3]benzazepine or 7-chloro-2-(3-chloropropyl)-3,4,5,6-tetrahydro-4-methylfuro[4,3,2-ef][3]benzazepine, is reacted with a nitrogen-containing heterocycle, such as 4-chloro-1H-pyrazole, in the presence of a base, such as sodium or potassium hydride, in a suitable solvent, such as dimethylformamide, to give formula (12) compounds.

Scheme V

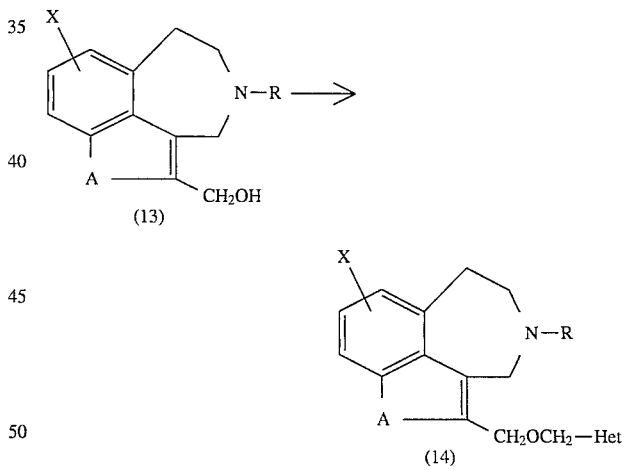

Scheme V shows the synthesis of compounds in which the Y-spacer group is —$CH_2$—E—$CH_2$, wherein E is —O—. According to Scheme V, the formula (13) 2-hydroxymethyl compound is alkylated with a heterocyclic-substituted alkyl halide, such as 4-chloro-1-(chloromethyl)-1H-pyrazole, 2-, 3- or 4-picolyl chloride, or 4-chloro-2-chloromethylpyridine, in the presence of a base, such as sodium or potassium hydride, in a suitable solvent, such as ethylene glycol dimethyl ether, to give formula (14) compounds.

The pharmaceutically acceptable, nontoxic, acid addition salts having the utility of the free bases of Formula (I), are formed with inorganic or organic acids, by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspattic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, and angina pectoris. Formula (I) compounds also are useful in treating peripheral vascular disease, particularly Raynaud's phenomenon and Raynaud's disease, benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

$Alpha_1$ adrenoceptor antagonist activity was determined using the rabbit aorta. Male New Zealand White rabbits (2–4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force-displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 mM) to block neuronal uptake and propranolol (1 mM) to block beta-adrenoceptors. Tissues were usually challenged once with norepinephrine (0.1 mM) during the equilibration period to check for viability.

A cumulative concentration-response curve to norepinephrine was obtained in each aortic segment. Following washout of norepinephrine, the a adrenoceptor antagonist to be tested was added to the bath. After the tissue had been in contact with the antagonist for 30–60 minutes, the norepinephrine concentration response-curve was repeated in the presence of antagonist. The tissue was then washed again, and a tenfold higher concentration of antagonist added. Following equilibration (30–60 minutes), a third norepinephrine concentration-response curve was determined in the presence of the antagonist.

The receptor dissociation constant ($K_\beta$) for the antagonist was determined using the relationship $$K_\beta = \frac{\text{Antagonist Concentration}}{\text{Dose Ratio} - 1}$$

(Furchgott, R. F., *Handbook of Experimental Pharmacology*, eds. Eichler, et al., pp. 283–335 (Springer 1972)). The $K_\beta$ value obtained at each antagonist concentration was averaged to obtain a mean $K_\beta$ for each experiment.

$Alpha_2$ adrenoceptor antagonist activity of the compounds was determined using the isolated, superfused guinea pig left atrium. Briefly, the heart is removed from a pentobarbital-anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known $\alpha_2$ agonist) is prepared by administering increasing concentrations of B-HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309:217–224 (1979).

$Alpha_3$ adrenoceptor antagonist receptor activity was determined using the dog saphenous vein (DSV) as the test system. This test system has been shown a suitable preparation in which to characterize postsynaptic $\alpha_2(\alpha_3)$ adrenoceptors, Sullivan, A. T. and G. M. Drew, *Arch. Pharmacol.*, 314:249–58 (1980). This test system is prepared by removing the lateral saphenous vein from an anesthetized dog and cutting the vein into segments of 4 mm in length. Segments are mounted as described for the isolated rabbit aorta.

The $\alpha_3$ adrenoceptor antagonist activity of the compounds of interest is determined by measuring shifts in the dose-response curve of a specific agonist induced by the tested compounds. The $\alpha_2$, $\alpha_3$ agonist, B-HT 920, was used in testing the compounds listed in Table I.

Representative Formula (I) compounds which are tested using the above described in vitro test systems are listed in Table I.

Table 1

5-(7-chloro-3,4,5,6-tetrahydro-4-methylthieno[4,3,2-ef][3]benzazepin-2-yl)oxazole;

5-(7-chloro-3,4,5,6-tetrahydro-4-methylfuro[4,3,2-ef][3]benzazepin-2-yl)oxazole;

2-(7-chloro-3,4,5,6-tetrahydro-4-methylfuro[4,3,2-ef][3]benzazepin-2-yl)-4,5-dihydro-1H-imidazole;

4-chloro-1-[(7-chloro-3,4,5,6-tetrahydro-4-methylfuro[4,3,2-ef][3]benzazepin-2-yl)methyl]-1H-pyrazole;

4-chloro-1-[3-(7-chloro-3,4,5,6-tetrahydro-4-methylfuro[4,3,2-ef][3]benzazepin-2-yl)propyl]-1H-pyrazole;

(E)-3-[(7-chloro-3,4,5,6-tetrahydro-4-methylfuro[4,3,2-ef][3]benzazepin-2-yl)methylene]dihyrdro-2(3H)furanone;

3-[(7-chloro-3,4,5,6-tetrahydro-4-methylfuro[4,3,2-ef][3]benzazepin-2-yl)methylene]-2-pyrrolidinone;

1-[3-(7-chloro-3,4,5,6-tetrahydro-4-methylfuro[4,3,2,-ef][3]benzazepin-2-yl)-1-oxo-2-propenyl]pyrrolidine;

(E)-1-[[2-(7-chloro-3,4,5,6-tetrahydro-4-methylfuro[4,3,2,-ef][3]benzazepin-2-yl)ethenyl]sulfonyl]pyrrolidine;

2-[2-(7-chloro-3,4,5,6-tetrahydro-4-methylfuro[4,3,2-ef][3]benzazepin-2-yl)-2-oxoethyl-4,5-dihydro-4,4-dimethyloxazole;

2-[2-(7-chloro-3,4,5,6-tetrahydro-4-methylfuro[4,3,2-ef][3]benzazepin-2-yl)-2-hydroxyethyl]-4,5-dihydro-4,4-dimethyloxazole;

2-[2-(7-chloro-3,4,5,6-tetrahydro-4-methylfuro[4,3,2-ef][3]benzazepin-2-yl)ethenyl]-4,5-dihydro-4,4-dimethyloxazole;

2-[2-(7-chloro-3,4,5,6-tetrahydro-4-methylthieno[4,3,2-ef][3]benzazepin-2-yl)-2-oxoethyl]-4,5-dihydro-4,4-dimethyloxazole;

2-[2-(7-chloro-3,4,5,6-tetrahydro-4-methylfuro[4,3,2-ef][3]benzazepin-2-yl)-2-oxoethyl]-4,5-dimethyloxazole;

2-[2-(7-chloro-3,4,5,6-tetrahydro-4-methylfuro[4,3,2-ef][3]benzazepin-2-yl)-2-hydroxyethyl-4,5-dimethyloxazole;

2-[2-(7-chloro-3,4,5,6-tetrahydro-4-methylfuro[4,3,2-ef][3]benzazepin-2-yl)ethenyl]-4,5-dimethyloxazole;

4-chloro-1-[2-(7-chloro-3,4,5,6-tetrahydro-4-methylfuro[4,3,2-ef][3]benzazepin-2-yl)methoxy]methyl]-1H-pyrazole;

(4-chloro-1H-pyrazol-1-yl)methyl 7-chloro-3,4,5,6-tetrahydro-4-methylfuro[4,3,2-ef][3]benzazepine-2-carboxylate;

2-[2-(7-chloro-3,4,5,6-tetrahydro-4-methylfuro[4,3,2-ef][3]benzazepin-2-yl)-2-hydroxyethyl]pyridine;

7-chloro-3,4,5,6-tetrahydro-4-methyl-2-[(2-pyridinylmethoxy)methyl]furo[4,3,2-ef][3]benzazepine;

7-chloro-2-[[(4-chloro-2-pyridinyl)methoxymethyl]-3,4,5,6-tetrahydro-4-methylfuro[4,3,2-ef][3]benzazepine;

7-chloro-3,4,5,6-tetrahydro-4-methyl-2-[(3-pyridinylmethoxy)methyl]furo[4,3,2-ef][3]benzazepine;

7-chloro-3,4,5,6-tetrahydro-4-methyl-2-[(4-pyridinylmethoxy)methyl]furo[4,3,2-ef][3]benzazepine;

2-pyridinylmethyl 7-chloro-3,4,5,6-tetrahydrofuro-4-methylfuro[4,3,2-ef][3]benzazepine-2-carboxylate;

2-[2-(7-chloro-3,4,5,6-tetrahydro-4-methylfuro[4,3,2-ef][3]benzazepin-2-yl)-2-hydroxyethyl]benzoxazole;

2-[2-(7-chloro-3,4,5,6-tetrahydro-4-methylfuro[4,3,2-ef][3]benzazepin-2-yl)ethenyl]benzoxazole;

2-[2-(7-chloro-3,4,5,6-tetrahydro-4-methylfuro[4,3,2-ef][3]benzazepin-2-yl)-2-oxoethyl]benzothiazole;

2-[2-(7-chloro-3,4,5,6-tetrahydro-4-methylfuro[4,3,2-ef][3]benzazepin-2-yl)-2-hydroxyethyl]benzothiazole;

2-[2-(7-chloro-3,4,5,6-tetrahydro-4-methylfuro[4,3,2-ef][3]benzazepin-2-yl)ethenyl]benzothiazole;

N-(2-benzothiazolyl)-7-chloro-3,4,5,6-tetrahydro-4-methylfuro[4,3,2-ef][3]benzazepine-2-carboxamide; and 2-[(7-chloro-3,4,5,6-tetrahydro-4-methylfuro[4,3,2-ef][3]benzazepin-2-yl)methylamino]benzothiazole;

or a pharmaceutically acceptable salt thereof.

The antihypertensive activity of Formula (I) compounds is determined using the spontaneously hypertensive rat model. The details of this in vivo test are found in Roesler, et at., *J. Pharmacol. Exp. Ther.*, 236:1–7 (1986).

The effect of Formula (I) compounds on peripheral vasculative is determined using Laser-Doppler flowmetry to continuously monitor changes in local cutaneous microvascular perfusion in pithed and anesthetized rats. This test is carried out according to the methods described in Willette, et al., *J. Pharmacol, Exp. Ther.*, 256:599–605 (1991) and in Willette, et al., *J. Auton. Nervous System*, 32:135–144 (1991).

The effect of Formula (I) compounds on proximal unethral perfusion pressure in the pithed rat is carried out according to the methods described in Willette, et al., *J. Pharmacol. Exp. Ther.* 252:706–710 (1990) and in Willette, et al., *J. Auton. Pharmacol.*, 9:63–70 (1989).

Novel pharmaceutical compositions are obtained when the compounds are incorporated with pharmaceutical careers into convenient dosage forms such as capsules, tablets, or injectable preparations. Solid or liquid pharmaceutical careers can be employed. Solid careers include, starch, lactose, calcium sulfate dihydrate, terra alba, sucrose, talc, gelatin, agar, pectin, acacia, magnesium stearate, and stearic acid. Liquid careers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in pharmaceutical dosage units will be an efficacious, nontoxic quantity selected from the range of 0.01–100 mg/kg of active compound, preferably 0.1–50 mg/kg. The selected dose is administered to a human patient in need of treatment from 1–6 times daily, orally, rectally, topically, by inhalation, or injection, or continuously by infusion. Oral administration, however, is preferred because it is more convenient for the patient.

The α-adrenoceptor antagonist compounds of this invention may also be administered stepwise or in physical combination with a second agent to treat the hereinbelow claimed indications. For example, Formula (I) compounds, preferably 5-(7-chloro-3,4,5,6-tetrahydro-4-methylthieno[4,3-ef][3]benzazepin-2-yl)oxazole, may be administered in combination with 5-α-reductase inhibitors, such as 17β-(N-t-butylcarbamoyl)-4-aza-5-α-androst-1-ene-3-one (U.S. Pat. No. 4,760,071) or 17β-(N-t-butylcarbamoyl)-androst-3,5-diene-3-carboxylic acid (U.S. Pat. No. 5,017,568), to treat benign prostatic hypertrophy (BPH).

The following examples are illustrative of preparation of Formula (I) compounds. The examples are not intended to limit the scope of the invention as defined hereinabove and as claimed below.

EXAMPLE 1

5-(7-Chloro-3,4,5,6-tetrahydro-4-methylthieno[4,3,2-ef][3]benzazepin-2-yl)oxazole A mixture of 7-chloro-3,4,5,6-tetrahydro-4-methylthieno[4,3,2-ef][3]benzazepine-2-carboxaldehyde (0.132 g, 0.5 mmol; U.S. Pat. No. 4,963,547), tosylmethyl isocyanide (0.0975 g, 5 mmol) and potassium carbonate (0.69 g, 5 mmol) in methanol (10 ml) was refluxed under argon for 2 h. The reaction mixture was filtered through Celite® and the solvent evaporated. Water was added to the residue and the resulting mixture was extracted with methylene chloride and the organic phase was washed, dried with magnesium sulfate and concentrated to give a tacky solid. The solid was dissolved in ether and treated with ethereal hydrogen chloride to give 5-(7-chloro-3,4,5,6-tetrahydro-4-methylthieno[4,3,2-ef][3]benzazepin-2-yl)oxazole hydrochloride: mp 268° C. (dec).

EXAMPLE 2

5-(7-Chloro-3,4,5,6-tetrahydro-4-methylfuro[4,3,2-ef][3]benzazepin-2-yl)oxazole

A mixture of 7-chloro-3,4,5,6-tetrahydro-4-methylfuro[4,3,2-ef][3]]benzazepine-2-carboxaldehyde (0.35 g, 1.39 mmol; U.S. Pat. No. 4,959,360), tosylmethyl-isocyanide (0.272 g, 1.39 mmol) and potassium carbonate (0.192 g, 1.39 mmol) in methanol (10 ml) was refluxed for 3 h under argon. The reaction mixture was poured into ice water and extracted with ethyl acetate. The ethyl acetate extract was washed with 2% hydrochloric acid and the aqueous phase was adjusted to pH 10 with 10% potassium carbonate, extracted with ethyl acetate and the organic phase washed with water, dried with magnesium sulfate, filtered and concentrated to give 300 mg of crude solid. The solid was recrystallized from ethanol and the resulting solid was dissolved in methylene chloride, warmed with carbon black (Darco), filtered through an acid washed silicon dioxide filtration agent (Celite®), and concentrated to give a solid which was stirred with methanol and filtered to give 82 mg (20.4%) of 5-(7-chloro-3,4,5,6-tetrahydro-4-methylfuro[4,3, 2-ef][3]benzazepin-2-yl)oxazole: mp 148.5°–149.5° C.

EXAMPLE 3

2-(7-Chloro-3,4,5,6-tetrahydro-4-methylfuro [4,3,2-ef][3]benzazepin-2-yl)- 4,5-dihydro-1H-imidazole Ethylenediamine (0.16 g, 2.7 mmol) in toluene (3 ml) was added dropwise to a solution of trimethylaluminum in toluene (2M, 1.35 ml, 2.7 mmol) stirred in an ice bath at a rate that maintained the reaction temperature between 0°–10° C. To this solution was added a solution of ethyl 7-chloro-3,4,5,6-tetrahydro-4-methylfuro[4,3,2-ef][3]benzazepine-2-carboxylate (0.5 g, 1.7 mmol; U.S. Pat. No. 4,959,360) in toluene (3 ml) at room temperature. The resulting solution was refluxed 3 hours under argon, cooled and the reaction mixture was quenched with water (3 ml), diluted with methanol (10 ml) and methylene chloride (10 ml) and refluxed for 15 minutes. The reaction mixture was filtered through a bed of sodium sulfate, concentrated and the residue was dissolved in ethyl acetate (40 ml) and refluxed for another 15 minutes, filtered through sodium sulfate and concentrated. The crude product was purified by thin layer chromatography on silica gel eluted with ethanol-methylene chloride (15:85) containing 0.25% triethylamine to give 0.2 g (41%) of 2-(7-chloro-3,4,5,6-tetrahydro-4-methylfuro[4,3,2-ef][3]benzazepin-2-yl)-4,5-dihydro-1H-imidazole dihydrochloride: mp>380° C. (dec).

EXAMPLE 4

4-Chloro-1-[(7-chloro-3,4,5,6-tetrahydro- 4-methylfuro[4,3,2-ef][3]benzazepin-2-yl)methyl]- 1H-pyrazole 1. 4-Chloro-1-[(7-chloro-4-ethoxycarbonyl-3,4,5,6-tetrahydrofuro[4,3,2-ef][3]benzazepin-2-yl)methyl]-1H-pyrazole A 60% dispersion of sodium hydride in mineral oil (0.72 g, 1.8 mmol) was washed with hexane and suspended in dry dimethylformamide (5 ml). To the above was added 4-chloro-1H-pyrazole (0.18 g, 1.75 mmol) and the resulting mixture was stirred at room temperature for 15 min. Then 2-bromomethyl-7-chloro-4-ethoxycarbonyl-3,4,5,6-tetrahydrofuro[4,3,2-ef][3]benzazepine (0.63 g, 1.7 mmol; U.S. Pat. No. 4,978,660) was added and the resulting suspension was stirred at room temperature overnight. The mixture was poured into water (50 ml) and extracted with ethyl ether. The ethereal solution was dried with magnesium sulfate, filtered, and concentrated. The crude product was crystallized from ethanol to give 4-chloro-1-[(7-chloro-4-ethoxycarbonyl-3,4, 5,6-tetrahydrofuro[4,3,2-ef][3]benzazepin-2-yl)methyl]-1H-pyrazole: mp 144°–147° C.

2. 4-Chloro-1-[(7-chloro-3,4,5,6-tetrahydro-4-methylfuro[4, 3,2-ef][3]benzazepin-2-yl)methyl]-1H-pyrazole To a suspension of lithium aluminum hydride (0.06 g, 1.6 mmol) in ethyl ether (15 ml) was added 4-chloro-1-[(7-chloro-4-ethoxycarbonyl-3,4,5,6-tetrahydrofuro[4,3,2-ef] [3]benzazepin-2-yl)methyl]-1H-pyrazole (0.32 g, 0.81 mmol). The resulting suspension was stirred at room temperature for 2 h and treated carefully with water (0.06 ml), 15% sodium hydroxide (0.06 ml) and water 0.12 ml). The resulting suspension was stirred for 20 min, filtered and concentrated. The resulting oil was purified by thin layer chromatography on silica gel eluted with ethanol-chloroform (10:90) and the fractions containing the product were combined, concentrated and the residue was dissolved in ethyl ether and treated with hydrogen chloride to give 0.06 g (22%) of 4-chloro-1-[(7-chloro-3,4,5,6-tetrahydro-4-methylfuro[4,3,2-ef][3]benzazepin-2-yl)methyl]-1H-pyrazole hydrochloride: mp 228°–230° C. (dec).

EXAMPLE 5

4-Chloro-1-[3-(7-chloro-3,4,5,6-tetrahydro- 4-methylfuro[4,3,2-ef][3]benzazepin-2-yl)propyl]- 1H-pyrazole To a suspension of potassium hydride (35% in mineral oil, 0.29 g, 2.5 mmol) in dimethylformamide (5 ml) was added 4-chloro-1H-pyrazole (0.24 g, 2.3 mmol). The resulting suspension was stirred at room temperature for 15 minutes and 7-chloro-2-(3-chloropropyl)-3,4,5,6-tetrahydro-4-methylfuro[4,3,2-ef][3]benzazepine (0.7 g, 2.3 mmol; U.S. Pat. No. 4,978,660) was added. The mixture was stirred overnight at room temperature under argon. The mixture was treated with water (50 ml) and extracted with ethyl ether. The organic phase was washed with water, dried with magnesium sulfate, filtered and concentrated. The crude product was purified by thin layer chromatography on silica gel eluted with ethanol-chloroform (10:90). The fractions containing the product were combined, concentrated, dissolved in ethyl ether and treated with hydrogen chloride to give 0.35 g (38%) of 4-chloro-1-[3-(7-chloro-3,4,5,6-tetrahydro-4-methylfuro[4,3,2-ef][3]benzazepin-2-yl)propyl]-1H-pyrazole hydrochloride: mp 225°–228° C.

EXAMPLE 6

(E)-3-[(7-Chloro-3,4,5,6-tetrahydro-4-methylfuro [4,3,2-ef][3]benzazepin-2-yl)methylene]-dihydro- 2(3H)furanone A suspension of sodium hydride (0.07 g, 2.8 mmol) in mineral oil was washed with hexane and suspended in dry toluene (10 ml). To the suspension was added α-diethylphosphono-γ-butyrolactone (0.62 g, 2.8 mmol) in dry toluene (2 ml). The mixture was stirred at 50° C. for 30 minutes, cooled to room temperature and a solution of 7-chloro-3,4,5,6-tetrahydro-4-methylfuro[4,3,2-ef][3]benzazepine-2-carboxaldehyde (0.7 g, 2.8 mmol; U.S. Pat. No. 4,959,360) was added dropwise. The resulting mixture was heated to 80° C. for 1.5 h, cooled to room temperature, filtered, concentrated and the resulting solid was dissolved in ethyl ether and treated with hydrogen chloride to give 0.45 g (45%) of (E)-3-[(7-chloro-3,4,5,6-tetrahydro-4-methylfuro[4,3,2-ef][3]benzazepin-2-yl)methylene]-dihyro-2(3H)furanone hydrochloride: mp >268° C. (dec)

EXAMPLE 7

3-[(7-Chloro-3,4,5,6-tetrahydro-4-methylfuro [4,3,2-ef][3]benzazepin-2-yl)methylene]- 2-pyrrolidinone A solution of N-acetyl-2-pyrrolidinone (0.48 g, 3.8 mmol) and 7-chloro-3,4,5,6-tetrahydro-4-methylfuro[4,3,2-ef][3] benzazepine-2-carboxaldehyde (0.95 g, 3.8 mmol; U.S. Pat. No. 4,959,360) in tetrahydrofuran (15 ml) was added dropwise to a suspension of sodium hydride (50% in mineral oil, 0.54 g, 11.3 mmol) in tetrahydrofuran (35 ml) stirred in an ice bath at a rate that maintained internal temperature between 5°–10° C. The mixture was stirred at 5° C. for 1 h, treated with methanol (2 ml) and concentrated. The residue was partitioned between methylene chloride and 3N hydrochloric acid, and the aqueous phase was basified to pH 8.5 with ammonium hydroxide and extracted with methylene chloride and chloroform. The organic phase was washed with water, dried with sodium sulfate and concentrated to give a solid that was crystallized from chloroform. The mother liquor was concentrated and the residue purified by thin layer chromatography on silica gel eluted with methanol-chloroform (10:90). The combined product was chromatographed on silica gel eluted with methanol-chloroform (10:90) and the residue dissolved in chloroform and treated with hydrogen chloride to give 3-[(7-3,4,5,6-tetrahydro-4-methylfuro[4,3,2-ef][3]benzazepin-2-yl)methylene]-2-pyrrolidinone hydrochloride: mp 296°–298° C. (dec).

EXAMPLE 8

1-[3-(7-Chloro-3,4,5,6-tetrahydrofuro[4,3,2-ef][3]benzazepin-2-yl)-1-oxo-2-propenyl]-4-methylpyrroldine To a suspension of (E)-3-(7-chloro-3,4,5,6-tetrahydro-4-methylfuro[4,3,2-ef][3]benzazepin-2-yl)-2-propenoyl chloride hydrochloride (0.5 g, 1.61 mmol; U.S. Pat. No. 4,959,360) in dimethylformamide (8 ml) was added triethylamine (0.5 ml, 3.54 mmol) followed by pyrrolidine (0.126 g, 1.77 mmol) in dimethylformamide (2 ml) dropwise. The resulting mixture was stirred overnight, filtered and the filtrate was washed with water. The organic phase was dried with magnesium sulfate, filtered and concentrated. The crude was purified by thin layer chromatography on silica gel eluted with methanol-chloroform (3:97) to give 0.13 g (21.6%) of 1-[3-(7-chloro-3,4,5,6-tetrahydro-4-methylfuro[4,3,2-ef][3]benzazepin-2-yl)-1-oxo-2-propenyl]pyrrolidine hydrochloride: mp 256°–257° C. (dec).

EXAMPLE 9

(E)-1-[[2-(7-Chloro-3,4,5,6-tetrahydrofuro[4,3,2-ef][3]benzazepin-2-yl)ethenyl]sulfonyl]-4-methylpyrrolidine Using the general procedure of Example 6, replacing α-diethylphosphono-γ-butyrolactone with [(diethylphosphono)methyl]sulfonylpyrrolidine [prepared from methylsulfonylpyrrolidine and diethylphosphochloridate according to the general procedure of J. Org. Chem., 47, 1284 (1982)] gave (E)-1-[[2-(7-chloro-3,4,5,6-tetrahydro-4-methylfuro[4,3,2-ef][3]benzazepin-2-yl)ethenyl]sulfonyl]pyrrolidine hydrochloride: mp 237° C. (dec).

EXAMPLE 10

2-[2-(7-Chloro-3,4,5,6-tetrahydro-4-methylfuro[4,3,2-ef][3]benzazepin-2-yl)-2-oxoethyl]-4,5-dihydro-4,4-dimethyloxazole To a cold solution of 4,5-dihydro-2,4,4-trimethyloxazole (1.5 ml, 12 mmol) in tetrahydrofuran (10 ml) at −78° C. was added, dropwise, a solution of butyllithium (2.6M, 4.65 ml, 12 mmol) in hexane followed by a solution of ethyl 7-chloro-3,4,5,6-tetrahydro-4-methylfuro[4,3,2-ef][3]benzazepine-2-carboxylate (3.2 g, 11 mmol; U.S. Pat. No. 4,959,360) in tetrahydrofuran (15 ml). The reaction mixture was warmed to room temperature during 1 h, quenched with ice-water, and extracted with ethyl ether. The organic phase was dried with magnesium sulfate, filtered and concentrated. The residue was triturated with hexane to yield 1.8 g (45.5%) of 2-[2-(7-chloro-3,4,5,6-tetrahydro-4-methylfuro[4,3,2-ef][3]benzazepin-2-yl)-2-oxoethyl]-4,5-dihydro-4,4-dimethyloxazole: mp 172°–173° C.

EXAMPLE 11

2-[2-(7-Chloro-3,4,5,6-tetrahydro-4-methylfuro[4,3,2-ef][3]benzazepin-2-yl)-2-hydroxyethyl]-4,5-dihydro-4,4-dimethyloxazole To a solution of 2-[2-(7-chloro-3,4,5,6-tetrahydro-4-methylfuro[4,3,2-ef][3]benzazepin-2-yl)-2-oxoethyl]-4,5-dihydro-4,4-dimethyloxazole (0.6 g, 1.66 mmol) in tetrahydrofuran (20 ml) was added sodium borohydride (0.25 g, 6.69 mmol). The resulting mixture was stirred 2 hours, concentrated and the residue partitioned between ethyl ether (50 ml) and water (30 ml). The organic phase was washed with water, dried with magnesium sulfate, filtered and concentrated. The residue was dissolved in methanol and purified by chromatography on silica eluted with methanol-methylene chloride (6:94) to yield 2-[2-(7-chloro-3,4,5,6-tetrahydro-4-methylfuro[4,3,2-ef][3]benzazepin-2-yl)-2-hydroxyethyl]-4,5-dihydro-4,4-dimethyloxazole.

EXAMPLE 12

2-[2-(7-Chloro-3,4,5,6-tetrahydro-4-methylfuro[4,3,2-ef][3]benzazepin-2-yl)ethenyl]-4,5-dihydro-4,4-dimethyloxazole Using the general procedure of Example 19, replacing 2-[2-(7-chloro-3,4,5,6-tetrahydro-4-methylfuro[4,3,2-ef][3]benzazePine-2-yl)-2-hydroxyethyl]benzoxazole with 2-[2-(7-chloro-3,4,5,6-tetrahydro-4-methylfuro[4,3,2-ef][3]benzazepin-2-yl)-2-hydroxyethyl]-4,5-dihydro-4,4-dimethyloxazole gave 2-[2-(7-chloro-3,4,5,6-tetrahydro-4-methylfuro[4,3,2-ef][3]benzazepin-2-yl)ethenyl]-4,5-dihydro-4,4-dimethyloxazole: mp 139.5°–142° C.

EXAMPLE 13

2-[2-(7-Chloro-3,4,5,6-tetrahydro-4-methylthieno[4,3,2-ef][3]benzazepine-2-yl)-2-oxoethyl]-4,5-dihydro-4,4-dimethyloxazole To a solution of 4,5-dihydro-2,4,4-trimethyloxazole (1.75 ml, 13.6 mmol) in tetrahydrofuran (12 ml) stirred at −78° C. was added butyllithium in hexane (2.5M, 5.44 ml, 13.62 mmol) dropwise. This mixture was kept at −78° C. for 2.5 h and then a cold solution of ethyl 7-chloro-3,4,5,6-tetrahydro-4-methylthieno[4,3,2-ef][3]benzazepine-2-carboxylate (4.2 g, 13.6 mmol; U.S. Pat. No. 4,963,547) in tetrahydrofuran (10 ml) was rapidly added. The resulting mixture was warmed to room temperature and stirred a further 40 min, partitioned between ice water and ethyl ether. The combined organic phase was washed with water and with brine, dried with magnesium sulfate, filtered and concentrated. The residue was chromatographed on aluminum oxide (activated, neutral) eluted with ethyl acetate-hexane. The fractions containing the product was pooled and concentrated. The solid was recrystallized from acetonitrile to yield 1.51 g (29.5%) of 2-[2-(7-chloro-3,4,5,6-tetrahydro-4-methylthieno[4,3,2-ef][3]benzazepine-2-yl)-2-oxoethyl-4,5-dihydro-4,4-dimethyloxazole: mp 133.5°–136° C.

EXAMPLE 14

2-[2-(7-Chloro-3,4,5,6-tetrahydro-4-methylfuro[4,3,2-ef][3]benzazepin-2-2-yl)-2-oxoethyl]-4,5-dimethyloxazole Using the general procedure of Example 10, replacing 4,5-dihydro-2,4,4-trimethyloxazole with 2,4,5-trimethyloxazole gave 2-[2-(7-chloro-3,4,5,6-tetrahydro-4-methylfuro[4,3,2-ef][3]benzazepin-2-yl)-2-oxoethyl]-4,5-dimethyloxazole mp 152°–153° C.

EXAMPLE 15

2-[2-(7-Chloro-3,4,5,6-tetrahydro-4-methylfuro[4,3,2-ef][3]benzazepin-2-yl)-2-hydroxyethyl]-4,5-dimethyloxazole To a stirred solution of 2-[2-(7-chloro-3,4,5,6-tetrahydro-4-methylfuro[4,3,2-ef][3]benzazepin-2-yl)-2-oxoethyl]-4,5-dimethyloxazole (0.5 g, 1.28 mmol) in methanol (30 ml) cooled to 0° C., was added sodium borohydride (0.75 g, 19.8 mmol) portionwise. The resulting mixture was stirred 2 h, quenched with water, and extracted with ethyl ether. The organic phase was washed with water, dried and concentrated to yield 0.48 g (86.9%) of 2-[2-(7-chloro-3,4,5,6-tetrahydro-4-methylfuro[4,3,2-ef][3]benzazepin-2-yl)-2-hydroxyethyl]-4,5-dimethyloxazole.

EXAMPLE 16

2-[2-(7-Chloro-3,4,5,6-tetrahydro-4-methylfuro[4,3,2-ef][3]benzazepin-2-yl)ethenyl]-4,5-dimethyloxazole Using the general procedure of Example 19, replacing 2-[2-(7-chloro-3,4,5,6-tetrahydro-4-methylfuro[4,3,2-ef][3]benzazepine-2-yl)-2-hydroxyethyl]benzoxazole with 2-[2-(7-chloro-3,4,5,6-tetrahydro-4-methylfuro[4,3,2-ef][3]benzazepin-2-yl)-2-hydroxyethyl]-4,5-dimethyloxazole gave 2-[2-(7-chloro-3,4,5,6-tetrahydro-4-methylfuro[4,3,2-ef][3]benzazepin-2-yl)ethenyl]-4,5-dimethyloxazole: mp 185°–187° C.

EXAMPLE 17

2-[2-(7-Chloro-3,4,5,6-tetrahydro-4-methylfuro[4,3,2-ef][3]benzazepin-2-yl)-2-hydroxyethyl]pyridine Using the procedure of Example 18, replacing 2-methylbenzoxazole with 2-picoline gave 2-[2-(7-chloro-3,4,5,6-tetrahydro-4-methylfuro[4,3,2-ef][3]benzazepin-2-yl)-2-hydroxyethyl]pyridine dihydrochloride: mp>260° C. (dec).

EXAMPLE 18

2-[2-(7-Chloro-3,4,5,6-tetrahydro-4-methylfuro[4,3,2-ef][3]benzazepin-2-yl)-2-hydroxyethyl]benzoxazole To a solution of 2-methylbenzoxazole (120 mg, 0.8 mmol) in tetrahydrofuran (40 ml) cooled to −72° C. and stirred under argon was added a solution of butyllithium in hexane (2.6M, 0.35 ml, 0.8 mmol). The resulting solution was stirred for 15 min and then 7-chloro-3,4,5,6-tetrahydro-4-methylfuro[4,3,2-ef][3]benzazepine-2-carboxaldehyde (0.2 g, 0.8 mmol; U.S. Pat. No. 4,959,360) in tetrahydrofuran (20 ml) was added. The mixture was stirred a further 15 min, warmed to room temperature and quenched with water. The phases were separated and the aqueous phase was extracted with ethyl ether. The combined organic phase was dried, filtered and concentrated. The residue was dissolved in ethyl ether and treated with ethereal hydrogen chloride to give the crude hydrochloride salt which was crystallized from methanol-ethyl ether to yield 55 mg (16.4%) of 2-[2-(7-chloro-3,4,5,6-tetrahydro-4-methylfuro[4,3,2-ef][3]-benzazepin-2-yl)-2-hydroxyethyl]benzoxazole hydrochloride.

EXAMPLE 19

2-[2-(7-Chloro-3,4,5,6-tetrahydro-4-methylfuro[4,3,2-ef][3]benzazepin-2-yl)ethenyl]benzoxazole To a solution of 2-[2-(7-chloro-3,4,5,6-tetrahydro-4-methylfuro[4,3,2-ef][3]benzazepin-2-yl)-2-hydroxyethyl]benzoxazole (0.4 g, 1.8 mmol) in methylene chloride (30 ml) containing triethylamine (4 ml) at 0° C. was added methanesulfonyl chloride (0.337 ml, 0.5 g). The resulting solution was stirred for 15 minutes, warmed to room temperature, quenched with water, washed with 5% sodium bicarbonate and with water, dried, concentrated and treated with hydrogen chloride to give 2-[2-(chloro-3,4,5,6-tetrahydro-4-methylfuro[4,3,2-ef][3]benzazepin-2-yl)ethenyl]benzoxazole hydrochloride: mp 275° C. (dec).

EXAMPLE 20

2-[2-(7-Chloro-3,4,5,6-tetrahydro-4-methylfuro[4,3,2-ef][3]benzazepin-2-yl)-2-oxoethyl]benzothiazole Using the general procedure of Example 10, replacing 4,5-dihydro-2,4,4-trimethyloxazole with 2-methylbenzothiazole gave 2-[2-(7-chloro-3,4,5,6-tetrahydro-4-methylfuro[4,3,2-ef][3]benzazepin-2-yl)-2-oxoethyl]benzothiazole: mp 200° C.

EXAMPLE 21

2-[2-(7-Chloro-3,4,5,6-tetrahydro-4-methylfuro[4,3,2-ef][3]benzazepin-2-yl)-2-hyroxyethyl]benzothiazole Using the general procedure of Example 18, replacing 2-methylbenzoxazole with 2-methylbenzothiazole, gave 2-[2-(7-chloro-3,4,5,6-tetrahydro-4-methylfuro[4,3,2-ef][3]benzazepin-2-yl)-2-hydroxyethyl]benzothiazole hydrochloride.

EXAMPLE 22

2-[2-(7-Chloro-3,4,5,6-tetrahydro-4-methylfuro[4,3,2-ef][3]benzazepin-2-yl)ethenyl]benzothiazole Using the general procedure of Example 19, replacing 2-[2-(7-chloro-3,4,5,6-tetrahydro-4-methylfuro[4,3,2-ef][3]benzazepine-2-yl)-2-hydroxyethyl]benzoxazole hydrochloride with 2-[2-(7-chloro-3,4,5,6-tetrahydro-4-methylfuro[4,3,2-ef][3]benzazepin-2-yl)-2-hydroxyethyl]benzothiazole hydrochloride gave 2-[2-(7-chloro-3,4,5,6-tetrahydro-4-methylfuro[4,3,2-ef][3]benzazepin-2-yl)ethenyl]benzothiazole: mp 184° C.

EXAMPLE 23

4-Chloro-1-[[2-(7-chloro-3,4,5,6-tetrahydro-
4-methylfuro[4,3,2-ef][3]benzazepin-2-yl)
methoxy]methyl]-1H -pyrazole To a stirred suspension of potassium hydride (35% in mineral oil, 0.16 g, 4 mmol) in ethylene glycol dimethyl ether (20 ml) was added a solution of 7-chloro-3,4,5,6-tetrahydro-4-methylfuro[4,3,2-ef][3]benzazepine-2-methanol (1.0 g, 4 mmol; U.S. Pat. No. 4,959,360) in ethylene glycol dimethyl ether (20 ml) dropwise at room temperature under argon. The suspension was stirred at room temperature for 20 min and then a solution of 4-chloro-1-(chloromethyl)-1H-pyrazole (0.6 g, 4 mmol) in ethylene glycol dimethyl ether (5 ml) was added. The resulting mixture was stirred at room temperature overnight, quenched with water (3 ml) and concentrated. The residue was partitioned between water and ethyl ether. The organic phase was dried with magnesium sulfate, filtered and concentrated. The resulting oil was chromatographed on silica gel eluted with 5% ethanol in chloroform. The fractions containing the product were pooled, concentrated and the resulting oil was dissolved in ethyl ether and treated with ethereal hydrogen chloride to give the hydrochloride salt which was recrystallized from acetone to give 0.65 g (40.6% ) of 4-chloro-1-[[2-(7-chloro-3,4,5,6-tetrahydro-4-methylfuro[4,3,2-ef][3]benzazepin-2-yl)methoxy]methyl]-1H-pyrazole hydrochloride :mp: 205°–206° C.

EXAMPLES 24–27

7-Chloro-3,4,5,6-tetrahydro-4-methyl-2-[(2-pyridinyl-
methoxy)methyl]furo[4,3,2-ef][3]benzazepine 7-Chloro-2-[[(4-chloro-2-pyridinyl)methoxy]methyl]-3,4,5,
6-tetrahydro-4-methylfuro[4,3,2-ef][3]benzazepine 7-Chloro-3,4,5,6-tetrahydro-4-methyl-2-[(3-pyridinyl-
methoxy)methyl]furo[4,3,2-ef][3]benzazepine 7-Chloro-3,4,5,6-tetrahydro-4-methyl-2-[(4-pyridinyl-
methoxy)methyl]furo[4,3,2-ef][3]benzazepine Using the general procedure of Example 23, replacing 4-chloro-1-(chloromethyl)-1H-pyrazole with 2-picolyl chloride hydrochloride, 4-chloro-2-chloromethylpyridine [Tetrahedron 38, 3277 (1982)], 3-picolyl chloride hydrochloride or 4-picolyl chloride hydrochloride gave:

7-chloro-3,4,5,6-tetrahydro-4-methyl-2-[(2-pyridinyl-
methoxy)methyl]furo[4,3,2-ef][3]benzazepine dihydrochloride: mp 206°–209° C.

7-chloro-2-[[(4-chloro-2-pyridinyl)methoxy]methyl]-3,4,5,
6-tetrahydro-4-methylfuro[4,3,2-ef][3]benzazepine dihydrochloride: mp 202.5°–203.5° C.

7-chloro-3,4,5,6-tetrahydro-4-methyl-2-[(3-pyridinyl-
methoxy)methyl]furo[4,3,2-ef][3]benzazepine dihydrochloride: mp 217°–220° C.

7-chloro-3,4,5,6-tetrahydro-4-methyl-2-[(4-pyridinyl-
methoxy)methyl]furo[4,3,2-ef][3]benzazepine dihydrochloride: mp 233°–235° C.

EXAMPLE 28

N-(2-Benzothiazolyl)-7-chloro-3,4,5,6-tetrahydro-
4-methylfuro[4,3,2-ef][3]benzazepine-2-carboxamide To a stirred suspension of 7-chloro-3,4,5,6-tetrahydro-4-methylfuro[4,3,2-ef][3]benzazepine-2-carbonyl chloride hydrochloride (0.32 g, 1 mmol; U.S. Pat. No. 4,978,660) and 2-aminobenzothiazole (0.155 g, 1 mmol) in toluene (4 ml) was added triethylamine (0.35 ml, 2.5 mmol). The resulting mixture was stirred at room temperature for 3.5 days and then heated at 50°–60° C. for 2 h, concentrated and the residue partitioned between water and ethyl acetate. The organic phase was washed with water and with brine and dried with magnesium sulfate, filtered and concentrated. The residue was dissolved in a small amount of methylene chloride and purified by thin layer chromatography on silica gel eluted with methanolmethylene chloride (2:98) containing a few drops of ammonium hydroxide. The product was eluted with tetrahydrofuran-ethyl acetate (2:1), concentrated and the resulting solid was recrystallized from tetrahydrofuran to give 47.8 mg (12%) of N-(2-benzothiazolyl)-7-chloro-3,4,5,6-tetrahydro-4-methylfuro[4,3,2-ef][3]benzazepine-2-carboxamide: mp 223°–225° C. (dec).

EXAMPLE 29

2-[(7-Chloro-3,4,5,6-tetrahydro-4-methylfuro
[4,3,2-ef][3]benzazepin-2-yl)
methylamino]benzothiazole To a stirred and refluxed suspension of lithium aluminum hydride (0.1934 g, 5.1 mmol) in tetrahydrofuran (25 ml) was added N-(2-benzothiazolyl)-7-chloro-3,4,5,6-tetrahydro-4-methylfuro[4,3,2-ef][3]benzazepine-2-carboxamide (0.754 g, 1.9 mmol). The resulting suspension was stirred for 2 h, cooled, quenched with water, treated with 10% sodium hydroxide, stirred, filtered, concentrated and dried by treatment with carbon tetrachloride followed by concentration. The crude product was purified by chromatography on silica gel eluted with methanol-chloroform (3:97) and recrystallized from ethyl acetate to give 0.21 g (29%) of 2-[(7-chloro-3,4,5,6-tetrahydro-4-methylfuro[4,3,2-ef][3]benzazepine-2-yl)methylamino]benzothiazole: mp 196.5°–200.5° C.(dec).

EXAMPLE 30

(4-Chloro-1H-pyrazol-1-yl)methyl
7-Chloro-3,4,5,6-tetrahydro-4-methylfuro
[4,3,2-ef][3]benzazepine-2-carboxylate A solution of 4-chloro-1H-pyrazole-1-methanol (46 mg, 0.034 mmol) in tetrahydrofuran (3 ml) was added to a suspension of 7-chloro-3,4,5,6-tetrahydro-4-methylfuro[4,3,2-ef][3]benzazepine-2-carbonyl chloride hydrochloride (100 mg, 0.32 mmol; U.S. Pat. No. 4,978,660) in tetrahydrofuran (6 ml) and triethylamine (0.09 ml, 0.63 mmol). The resulting mixture was heated at 60° C. for 2.5 h and concentrated. The residue was dissolved in methylene chloride and washed with water. The organic phase was dried with magnesium sulfate and sodium sulfate, filtered and concentrated. The solid was chromatographed twice on silica gel plate eluted with ethyl acetate-hexane (60:40). Fractions containing the product were combined, concentrated and the resulting solid was dissolved in ethyl ether and treated with ethereal hydrogen chloride to give 28 mg (26%) of (4-chloro-1H-pyrazol-1-yl)methyl 7-chloro-3,4,5,6-tetrahydro-4-methylfuro[4,3,2,ef]-[3]benzazepine-2-carboxylate hydrochloride: mp 154°–155° C. (dec).

EXAMPLE 31

2-Pyridinylmethyl
7-Chloro-3,4,5,6-tetrahydrofuro-4-methylfuro
[4,3,2-ef][3]benzazepine-2-carboxylate Using the general procedure of Example 30, replacing 4-chloro-1H-pyrazole-1-methanol with 2-pyridinylmethanol gave 2-pyridinylmethyl 7-chloro-3,4,5,6-tetrahydro-4-meth-

23 ylfuro[4,3,2-ef][3]benzazepine-2-carboxyl dihydrochloride: top: 247° C. (dec).

EXAMPLE 32

5-(7-Chloro-3,4,5,6-tetrahydro-thieno[4,3,2-ef][3]benzazepin-2-yl)oxazole

A solution of 5-(7-Chloro-3,4,5,6-tetrahydro-4-methylthieno[4,3,2-ef][3]benzazepin-2-yl)oxazole, prepared in Example 1, in 1,2-dichloroethane is treated with 2,2,2-trichloroethyl chloroformate and the mixture is heated to reflux. The mixture is evaporated and the residue is dissolved in tetrahydrofuran and acetic acid and treated with zinc powder. The resulting suspension is stirred, filtered and concentrated to give 5-(7-chloro-3,4,5,6-tetrahydro-thieno[4,3,2-ef][3]benzazepin-2-yl)oxazole.

EXAMPLE 33

An oral dosage form for administering the presently invented compounds is produced by screening, mixing, and filling into a hard gelatin capsule ingredients in the proportions shown in Table II, below.

TABLE II

| Ingredients | Amounts |
| --- | --- |
| 5-(7-chloro-3,4,5,6-tetrahydro-4-methylthieno[4,3,2-ef][3]benzazepin-2-yl)oxazole | 50 mg |
| magnesium stearate | 5 mg |
| lactose | 75 mg |

EXAMPLE 34

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| 5-(7-chloro-3,4,5,6-tetrahydro-4-methylthieno[4,3,2-ef][3]benzazepin-2-yl)oxazole | 100 mg |
| calcium sulfate dihydrate | 150 mg |
| sucrose | 20 mg |
| starch | 10 mg |
| talc | 5 mg |
| stearic acid | 3 mg |

EXAMPLE 35

5-(7-chloro-3,4,5,6-tetrahydro-4-methylthieno[4,3,2-ef][3]benzazepin-2-yl)oxazole, 75 mg, is dispersed in 25 ml of normal saline to prepare an injectable preparation.

While the preferred embodiments of the invention are illustrated by the above, the invention is not limited to the precise instructions herein disclosed and that the right to all modifications coming within the scope of the following claims is reserved.

24

What is claimed is:
1. A compound of the formula:

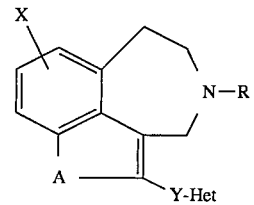

in which:

X is H, Cl, Br, F, I, $CF_3$, $C_{1-6}$ alkyl, $COR^1$, $CO_2R^2$, $CONR^2R^2$, CN, $NO_2$, $NR^2R^3$, $OR^3$, $SC_{1-4}$ alkyl, $S(CH_2)_{0-6}$ phenyl, $SCF_3$, or any accessible combination thereof of up to three substituents;

R is H, $C_{1-6}$ alkyl, or $C_{3-5}$ alkenyl;

each $R^1$ independently is $C_{1-6}$ alkyl or $(CH_2)_{0-6}$ phenyl;

each $R^2$ independently is H, $C_{1-6}$alkyl, or $(CH_2)_{0-6}$phenyl;

each $R^3$ independently is H, $C_{1-6}$ alkyl, $(CH_2)_{0-6}$ phenyl, $COR^1$, or $SO_2R^1$;

A is O or S;

Y is a single bond, $-(CH_2)_{1-4}-$, $-CH=$, $-CH=CH-Q-$, or $-(CH_2)_{0-2}-E-(CH_2)_{0-2}-$;

Q is a single bond, $-SO_2-$ or $-C(O)-$;

E is $-CH(OH)-$, $-C(O)-$, $-O-$, $-S-$, $-CO_2-$, $-NR^2-$, or $-C(O)NR^2-$; and Het is a stable 5- to 7-membered monocyclic or 7- to 10-membered bicyclic heterocyclic ring, which is either saturated or unsaturated, and which consists of carbon atoms and from one to three heteroatoms selected from the group consisting of N, O, S, wherein the nitrogen and sulfur atoms may optionally be oxidized, and the nitrogen heteroatom may optionally be quaternized, and the carbon atoms may optionally be doubly bonded to oxygen, and including any bicyclic group in which any of the above-defined heterocyclic rings is fused to a benzene ring and wherein the Het is unsubstituted or substituted by any accessible combination thereof of up to three substituents selected from the group consisting of $C_1-C_6$alkyl, $C_1-C_6$alkoxy, Cl, Br, F, I, $CF_3$ $NR^2R^2$, $CO_2R^2$, $CONR^2R^2$, $SO_3H$, $SO_2NHR^2$, OH, $NO_2$, $SO_2C_1-C_6$alkyl, $SC_1-C_6$alkyl, or $NR^2COC_1-C_6$alkyl;

or a pharmaceutically acceptable salt thereof.

2. The compound according to claim 1 of the formula:

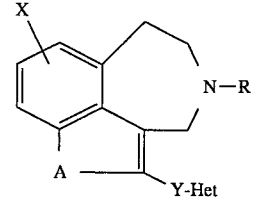

in which:

X is H, Cl, Br, F, I, $CF_3$, $C_{1-6}$ alkyl, $COR^1$, $CO_2R^2$, $CONR^2R^2$, CN, $NO_2$, $NR^2R^3$, OR, $SC_{1-4}$ alkyl, $S(CH_2)_{0-6}$ phenyl, or $SCF_3$;

R is H, $C_{1-6}$ alkyl, or $C_{3-5}$ alkenyl;

each $R_1$ independently is $C_{1-6}$ alkyl or $(CH_2)_{0-6}$ phenyl;

each $R^2$ independently is H, $C_{1-6}$alkyl, or $(CH_2)_{0-6}$phenyl;

each $R^3$ independently is H, $C_{1-6}$ alkyl, $(CH_2)_{0-6}$ phenyl, $COR^1$, or $SO_2R^1$;

A is O or S;

Y is a single bond, —$(CH_2)_{1-4}$—, —CH=, —CH=CH—Q—, or —$(CH_2)_{0-2}$—E—$(CH_2)_{0-2}$—;

Q is a single bond, —$SO_2$— or —C(O)—;

E is —CH(OH)—, —C(O)—, —O—, —S—, —$CO_2$—, —$NR^2$—, or —$C(O)NR^2$—; and

Het is a stable 5- to 7-membered monocyclic or 7- to 10-membered bicyclic heterocyclic ring, which is either saturated or unsaturated, and which consists of carbon atoms and from one to three heteroatoms selected from the group consisting of N, O, S, wherein the nitrogen and sulfur atoms may optionally be oxidized, and the nitrogen heteroatom may optionally be quaternized and the carbon atoms may optionally be doubly bonded to oxygen, and including any bicyclic group in which any of the above-defined heterocyclic rings is fused to a benzene ring and wherein the Het is unsubstituted or substituted by any accessible combination thereof of up to three substituents selected from the group consisting of $C_1$-$C_6$alkyl, $C_1$-$C_6$alkoxy, Cl, Br, F, I, $CF_3$ $NR^2R^2$, $CO_2R^2$, $CONR^2R^2$, $SO_3H$, $SO_2NHR^2$, OH, $NO_2$, $SO_2C_1$-$C_6$alkyl, $SC_1$-$C_6$alkyl, or $NR^2COC_1$-$C_6$alkyl;

or a pharmaceutically acceptable salt thereof.

3. The compound according to claim 2 wherein Het is oxazolyl, dihydrooxazolyl, pyridinyl, benzothiazolyl, benzoxazolyl, indolyl, benzimidazolyl, imidazolyl, dihydroimidazolyl, pyrrolidinyl, pyrrolidin-one-yl, pyrrolyl, thienyl, furanyl, tetrahydrofuranyl, oxotetrahydrofuranyl, pyrazolyl, triazolyl, pyridazinyl, pyrimidinyl, pryazinyl, thiazolyl, tetrazolyl, benzofuranyl, benxothienyl, quinolyl, or isoquinolyl, and each Het is unsubstituted or substituted by any accessible combination thereof of up to two substitutents selected from the group consisting of $C_{1-6}$alkyl, Cl, Br, F, I, or $CF_3$.

4. The compound according to claim 3 wherein X is Cl, Br, F, or I.

5. The compound according to claim 4 wherein R is $C_{1-6}$alkyl.

6. The compound according to claim 5 wherein Het is oxazolyl, dihydrooxazolyl, imidazolyl, dihydroimidazolyl, pyrrolidinyl, pyrrolidin-one-yl, pyrrolyl, thienyl, furanyl, tetrahydrofuranyl, oxotetrahydrofuranyl, pyrazolyl, triazolyl, thiazolyl, or tetrazolyl and each Het is unsubstituted or substituted by any accessible combination thereof of up to two substituents selected from the group consisting of $C_{1-6}$alkyl, Cl, Br, F, I, or $CF_3$.

7. The compound according to claim 6 which is 5-(7-chloro-3,4,5,6-tetrahydro-4-methylthieno[4,3,2-ef][3]benzazepin-2-yl)oxazole or a pharmaceutically acceptable salt thereof.

8. The compound according to claim 6 which is:
5-(7-chloro-3,4,5,6-tetrahydro-4-methylfuro[4,3,2-ef][3]benzazepin-2-yl)oxazole;
2-(7-chloro-3,4,5,6-tetrahydro-4-methylfuro[4,3,2-ef][3]benzazepin-2-yl)-4,5-dihydro-1H-imidazole;
4-chloro-1-[(7-chloro-3,4,5,6-tetrahydro-4-methylfuro[4,3,2-ef][3]benzazepin-2-yl)methyl]-1H-pyrazole;
4-chloro-1-[3-(7-chloro-3,4,5,6-tetrahydro-4-methylfuro[4,3,2-ef][3]benzazepin-2-yl)propyl]-1H-pyrazole;
(E)-3-[(7-chloro-3,4,5,6-tetrahydro-4-methylfuro[4,3,2-ef][3]benzazepin-2-yl)methylene]dihyrdro-2(3H)furanone;
3-[(7-chloro-3,4,5,6-tetrahydro-4-methylfuro[4,3,2-ef][3]benzazepin-2-yl)methylene]-2-pyrrolidinone;
1-[3-(7-chloro-3,4,5,6-tetrahydro-4-methylfuro[4,3,2,-ef][3]benzazepin-2-yl)-1-oxo-2-propenyl]pyrrolidine;
(E)-1-[[2-(7-chloro-3,4,5,6-tetrahydro-4-methylfuro[4,3,2,-ef][3]benzazepin-2-yl)ethenyl]sulfonyl]pyrrolidine;

2-[2-(7-chloro-3,4,5,6-tetrahydro-4-methylfuro[4,3,2-ef][3]benzazepin-2-yl)-2-oxoethyl-4,5-dihydro-4,4-dimethyloxazole;
2-[2-(7-chloro-3,4,5,6-tetrahydro-4-methylfuro[4,3,2-ef][3]benzazepin-2-yl)-2-hydroxyethyl]-4,5-dihydro-4,4-dimethyloxazole;
2-[2-(7-chloro-3,4,5,6-tetrahydro-4-methylfuro[4,3,2-ef][3]benzazepin-2-yl)ethenyl]-4,5-dihydro-4,4-dimethyloxazole;
2-[2-(7-chloro-3,4,5,6-tetrahydro-4-methylthieno[4,3,2-ef][3]benzazepin-2-yl)-2-oxoethyl]-4,5-dihydro-4,4-dimethyloxazole;
2-[2-(7-chloro-3,4,5,6-tetrahydro-4-methylfuro[4,3,2-ef][3]benzazepin-2-yl)-2-oxoethyl]-4,5-dimethyloxazole;
2-[2-(7-chloro-3,4,5,6-tetrahydro-4-methylfuro[4,3,2-ef][3]benzazepin-2-yl)-2-hydroxyethyl]-4,5-dimethyloxazole;
2-[2-(7-chloro-3,4,5,6-tetrahydro-4-methylfuro[4,3,2-ef][3]benzazepin-2-yl)ethenyl]-4,5-dimethyloxazole;
4-chloro-1-[2-(7-chloro-3,4,5,6-tetrahydro-4-methylfuro[4,3,2-ef][3]benzazepin-2-yl)methoxy]methyl]-1H-pyrazole; or
(4-chloro-1H-pyrazol-1-yl)methyl 7-chloro-3,4,5,6-tetrahydro-4-methylfuro[4,3,2-ef][3]benzazepine-2-carboxylate;
or a pharmaceutically acceptable salt thereof.

9. The compound according to claim 5 wherein Het is pyridinyl, pyridazinyl, pyrimidinyl, or pyrazinyl, and each Het is unsubstituted or substituted any accessible combination thereof of up to two substitutents selected from the group consisting of $C_{1-6}$alkyl, Cl, Br, F, I, or $CF_3$.

10. The compound according to claim 9 which is:
2-[2-(7-chloro-3,4,5,6-tetrahydro-4-methylfuro[4,3,2-ef][3]benzazepin-2-yl)-2-hydroxyethyl]pyridine;
7-chloro-3,4,5,6-tetrahydro-4-methyl-2-[(2-pyridinylmethoxy)methyl]furo[4,3,2-ef][3]benzazepine;
7-chloro-2-[(4-chloro-2-pyridinyl)methoxymethyl]-3,4,5,6-tetrahydro-4-methylfuro[4,3,2-ef][3]benzazepine;
7-chloro-3,4,5,6-tetrahydro-4-methyl-2-[(3-pyridinylmethoxy)methyl]furo[4,3,2-ef][3]benzazepine;
7-chloro-3,4,5,6-tetrahydro-4-methyl-2-[(4-pyrindinylmethoxy)methyl]furo[4,3,2-ef][3]benzazepine; or
2-pyridinylmethyl 7-chloro-3,4,5,6-tetrahydrofuro-4-methylfuro[4,3,2-ef][3]benzazepine-2-carboxylate; or a pharmaceutically acceptable salt thereof.

11. The compound according to claim 5 wherein Het is benzothiazolyl, benzoxazolyl, indolyl, or benzimidazolyl benzofuranyl, benzothienyl, quinolyl, or isoquinolyl and each Het is unsubstituted or substituted by any accessible combination thereof of up to two substituents selected from the group consisting of $C_{1-6}$alkyl, Cl, Br, F, I, or $CF_3$.

12. The compound according to claim 11 which is:
2-[2-(7-chloro-3,4,5,6-tetrahydro-4-methylfuro[4,3,2-ef][3]benzazepin-2-yl)-2-hydroxyethyl]benzoxazole;
2-[2-(7-chloro-3,4,5,6-tetrahydro-4-methylfuro[4,3,2-ef][3]benzazepin-2-yl)ethenyl]benzoxazole;
2-[2-(7-chloro-3,4,5,6-tetrahydro-4-methylfuro[4,3,2-ef][3]benzazepin-2-yl)-2-oxoethyl]benzothiazole;
2-[2-(7-chloro-3,4,5,6-tetrahydro-4-methylfuro[4,3,2-ef][3]benzazepin-2-yl)-2-hydroxyethyl]benzothiazole;
2-[2-(7-chloro-3,4,5,6-tetrahydro-4-methylfuro[4,3,2-ef][3]benzazepin-2-yl)ethenyl]benzothiazole;
N-(2-benzothiazolyl)-7-chloro-3,4,5,6-tetrahydro-4-methylfuro[4,3,2-ef][3]benzazepine-2-carboxamide; or
2-[(7-chloro-3,4,5,6-tetrahydro-4-methylfuro[4,3,2-ef][3]benzazepin-2-yl)methylamino]benzothiazole;
or a pharmaceutically acceptable salt thereof.

13. A pharmaceutical composition comprising a compound according to claim 1 and a pharmaceutically acceptable carrier.

14. A pharmaceutical composition comprising a compound according to claim 7 and a pharmaceutically acceptable carrier.

15. A method of antagonizing α-adrenergic receptors in mammals that comprises administering to a subject in need thereof an effective amount of a compound of claim 1.

16. A method of antazonizing α-adrenergic receptors in mammals that comprises administering to a subject in need thereof an effective amount of a compound of claim 7.

17. A method of treating benign prostatic hypertrophy in mammals that comprises administering to a subject in need thereof an effective amount of a compound of claim 1.

18. A method of treating benign prostatic hypertrophy in mammals that comprises administering to a subject in need thereof an effective amount of a compound of claim 7.

19. A method of treating peripheral vascular disease in mammals that comprises administering to a subject in need thereof an effective amount of a compound of claim 1.

20. A method of treating peripheral vascular disease in mammals that comprises administering to a subject in need thereof an effective amount of a compound of claim 7.

21. A method of treating congestive heart failure in mammals that comprises administering to a subject in need thereof an effective amount of a compound of claim 1.

22. A method of treating congestive heart failure in mammals that comprises administering to a subject in need thereof an effective amount of a compound of claim 7.

23. A method of treating hypertension in mammals that comprises administering to a subject in need thereof an effective amount of a compound of claim 1.

24. A method of treating hypertension in mammals that comprises administering to a subject in need thereof an effective amount of a compound of claim 7.

* * * * *